(12) United States Patent
Adkins et al.

(10) Patent No.: US 12,396,937 B2
(45) Date of Patent: Aug. 26, 2025

(54) OINTMENTS FOR TREATING DRY SKIN

(71) Applicant: OCuSOFT, Inc., Rosenberg, TX (US)

(72) Inventors: Nat Adkins, Rosenberg, TX (US); Troy Smith, Rosenberg, TX (US); Paramita Sarkar, Rosenberg, TX (US); Brandon Sands, Rosenberg, TX (US)

(73) Assignee: OCuSOFT, Inc., Rosenberg, TX (US)

( * ) Notice: Subject to any disclaimer, the term of this patent is extended or adjusted under 35 U.S.C. 154(b) by 238 days.

(21) Appl. No.: 17/945,311

(22) Filed: Sep. 15, 2022

(65) Prior Publication Data

US 2023/0078553 A1 Mar. 16, 2023

Related U.S. Application Data

(60) Provisional application No. 63/244,512, filed on Sep. 15, 2021.

(51) Int. Cl.
| | |
|---|---|
| *A61K 8/41* | (2006.01) |
| *A61K 8/04* | (2006.01) |
| *A61K 8/31* | (2006.01) |
| *A61K 8/34* | (2006.01) |
| *A61K 8/86* | (2006.01) |
| *A61Q 19/00* | (2006.01) |

(52) U.S. Cl.
CPC ............... *A61K 8/41* (2013.01); *A61K 8/042* (2013.01); *A61K 8/31* (2013.01); *A61K 8/345* (2013.01); *A61K 8/86* (2013.01); *A61Q 19/007* (2013.01)

(58) Field of Classification Search
CPC . A61K 8/41; A61K 8/042; A61K 8/31; A61K 8/345; A61K 8/86; A61Q 19/007
See application file for complete search history.

(56) References Cited

U.S. PATENT DOCUMENTS

| | | | |
|---|---|---|---|
| 4,348,415 A * | 9/1982 | Tsutsumi | A61Q 19/00 514/975 |
| 5,683,683 A | 11/1997 | Scafidi | |
| 2004/0170591 A1* | 9/2004 | Allart | A61P 17/00 514/355 |
| 2011/0044920 A1 | 2/2011 | Hines et al. | |
| 2011/0218350 A1* | 9/2011 | Selifonov | C07D 307/20 554/213 |
| 2014/0274982 A1 | 9/2014 | Bakan et al. | |
| 2015/0111923 A1 | 4/2015 | Amselem et al. | |
| 2016/0184245 A1 | 6/2016 | Eberting | |
| 2021/0093539 A1 | 4/2021 | Larosa et al. | |

FOREIGN PATENT DOCUMENTS

| | | |
|---|---|---|
| EP | 0995424 A2 | 4/2000 |
| JP | 2000026271 A | 1/2000 |
| KR | 101658361 B1 | 9/2016 |
| KR | 20180023537 A | 3/2018 |
| WO | 2020230691 A1 | 11/2020 |

OTHER PUBLICATIONS

JP2016222585A, Machine translation (Year: 2016).*
Bergfield et al (Year: 2015).*
JP2000026271A, Machine Translation (Year: 2000).*

* cited by examiner

*Primary Examiner* — Jeffrey S Lundgren
*Assistant Examiner* — Ibrahim D Bori
(74) *Attorney, Agent, or Firm* — D'Ambrosio & Menon, PLLC; Usha Menon

(57) ABSTRACT

A composition for treating dry skin includes therapeutically active concentrations of one or more skin protecting lipids in an oleaginous base. The skin protecting lipids can include a sphingolipid and at least one oil. The composition is intended for application on the skin surrounding the eyes. The composition is configured to form a protective, occlusive layer that can moisturize the skin and reduce inflammation and itching without stinging, burning, or stripping the skin. According to an exemplary embodiment, the composition is formulated as a high viscosity ointment or gel.

15 Claims, No Drawings

OINTMENTS FOR TREATING DRY SKIN

CROSS-REFERENCE TO RELATED APPLICATION

This application claims the benefit of Provisional U.S. Patent Application No. 63/244,512, filed Sep. 15, 2021, entitled "COMPOSITIONS FOR TREATING DRY SKIN", the entire content and disclosure of which, both express and implied, is incorporated herein by reference.

FIELD OF THE INVENTION

The present invention relates generally to compositions for treating dry skin, and specifically to ointments for treating dry skin surrounding the eyes, including, the eyelids and eyelid margins and to methods of preparing and using such ointments.

BACKGROUND

Ocular health refers to eyes as well as structures associated with the eyes, eyelids for example. The eyelids are important in over-all ocular health because they protect the eyes from dangers such as approaching objects or from airborne contaminants, such as pollen, dust particles or other foreign bodies. The eyelids contain essential glands; the lacrimal glands and meibomian glands that produce layers of tear film that are critical for healthy eyes. When an individual blinks, a new tear film is created, and tears are distributed across the cornea to lubricate the surface of the eye. This blinking action also "flushes" foreign materials from the eye.

The skin on the eyelids and in the ocular region is very thin and much more sensitive than the skin on the other parts of the body. It is unable to readily retain moisture and is highly susceptible to dryness and irritation. Dryness of the eyelids and in the ocular region can be caused by a variety of factors, including physiological conditions such as atopic dermatitis or rosacea, allergens, contact dermatitis and environmental conditions. Aging causes the skin to lose moisture and become thinner and drier. Also, the fat below the skin surrounding the eyes is lost, which makes that area extra fragile and more likely to flake and become irritated.

While some people with dry skin in and around the ocular area may experience only mild to no discomfort, many others experience more intense irritation that can worsen during blinking. Dryness of the eyelids, if left untreated, may lead to extreme discomfort, irritation, inflammation, and itchiness.

Often people will resort to rubbing dry, irritated, itchy skin to relieve discomfort. However, eye rubbing, or scratching should be avoided because it can damage not only the eyelid skin, leaving the eye susceptible to foreign dangers such as approaching objects or airborne contaminants, but also the lens and/or the cornea. Moisturizers can reduce the chance of developing extreme dryness and can combat skin discomfort and irritation.

Furthermore, dryness of the eyelids can be exacerbated and can develop into blepharitis. Blepharitis is a common condition in which the eyelid margins are persistently inflamed. With blepharitis, one can experience discomfort, inflammation, dryness, and itching of the eyelids. The condition may be caused by a bacterial infection, or it may be allergic in origin or associated with seborrhea of the face and scalp.

Eyelid dermatitis is a common condition that causes the skin on or around the eyelid to become dry, itchy, and irritated. Often this condition extends to other parts of the periorbital area, particularly under the eye. While the causes of this condition are various, including psoriasis, seborrhea, rosacea, contact urticaria, atopic dermatitis and contact dermatitis, treatment of eyelid dermatitis can be problematic because the eyelid and other periorbital skin is naturally thin and moist. Eyelid skin is, moreover, occluded because it retracts when the lid is open.

Dry, irritated skin can also be treated with moisturizers. Moisturizers can reduce the chance of developing extreme dryness and can combat skin discomfort and irritation. Often, moisturizers contain ingredients and chemicals which are unsuitable for application in the ocular region. For example, hydrocortisone cream can be used to treat irritation of the skin, including on the face. However, hydrocortisone cream is generally too harsh to be used on the eyelid or in the ocular region. Thus, the sensitivity can make it difficult to find a quick-acting, soothing delivery of key components to relieve dry skin, discomfort, and irritation while also being mild enough for ocular region application. Therefore, there is a need for a composition that can form a protective, occlusive layer while delivering moisturizing emollients to combat eyelid skin discomfort.

SUMMARY

According to an embodiment, the invention is a topical gel or ointment comprising a dermatologically acceptable vehicle and a plurality of ingredients dissolved in the vehicle. The dermatologically acceptable vehicle can be an oleaginous base or an aqueous base. In one exemplary embodiment, the ointment includes a lipid mixture comprising a sphingolipid and at least one oil in a white petrolatum base. The sphingolipid can be selected from the group consisting of phytosphingosine, phytosphingosine HCl, dihydrosphingosine, sphingosine, sphingomyelins, glycosphingolipids, and derivatives and mixtures thereof. The oil can be selected from the group consisting of castor oil, caprylic/capric triglyceride, ethyl oleate, isopropyl myristate, isopropyl palmitate, isopropyl isostearate, isostearyl isostearate, argan oil, and derivatives and mixtures thereof. The ointment can further include at least one hydrophilic solvent and an emulsifier. The hydrophilic solvent can be selected from the group consisting of glycerin, propylene glycol, and DL-panthenol and derivatives and mixtures thereof. The emulsifier can be selected from the group consisting of PEG-150 distearate, PEG-150 Pentaerythrityl Tetrastearate, Disteareth-75 IPDI and derivatives and mixtures thereof.

In one or more embodiments, the ointment can include white petrolatum in the range of about 65% to 75% by weight; a sphingolipid in the range of about 0.25% to 1% by weight; an oil in the range of about 15% to 30% by weight; a hydrophilic solvent in the range of about 1% to 5% by weight, and an emulsifier in the range of about 1% to 10% by weight of the composition.

According to an exemplary embodiment, a composition for treating dry skin comprises a white petrolatum base, a lipid mixture of phytosphingosine HCL and castor oil, propylene glycol, and PEG-150 distearate. The composition is preferably in the form of an ointment or a gel.

In an embodiment, the ointment can further include one or more ingredients selected from the group consisting of surfactants, viscosity agents, preservatives, antioxidants, chelating agents, buffers, and mixtures thereof. The ointment can further include one or more medicinal, antiallergic, and anti-inflammatory agents.

The ointment is formulated as a high viscosity ointment or gel. The ointment can have a viscosity in the range of 10.0 to 50,000 cps, and a pH between 3.0 and 9.0.

In another embodiment, a method of treating dry skin involves administering an effective amount of the topical ointment.

DETAILED DESCRIPTION

The term and phrases "invention," "present invention," "instant invention," and similar terms and phrases as used herein are non-limiting and are not intended to limit the present subject matter to any single embodiment, but rather encompass all possible embodiments as described.

As used herein, all weight percentages (wt. %) are based on the total wt. % of the skin care composition, unless otherwise specified. Additionally, all composition percentages are based on totals equal to 100 wt. %, unless otherwise specified.

The compositions and methods for their use can "comprise," "consist essentially of," or "consist of" any of the ingredients or steps disclosed throughout the specification. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and can include the ingredients of the present invention and do not exclude other ingredients or elements described herein. The use of the word "a" or "an" when used in conjunction with the term "comprising" in the claims and/or the specification may mean "one," but it is also consistent with the meaning of "one or more," "at least one," and "one or more than one." As used herein, "consisting essentially of" means that the invention may include ingredients in addition to those recited in the claims, but only if the additional ingredients do not materially alter the basic and novel characteristics of the claimed invention. Generally, such additives may not be present at all or only in trace amounts. However, it may be possible to include up to about 10% by weight of materials that could materially alter the basic and novel characteristics of the invention as long as the utility of the composition (as opposed to the degree of utility) is maintained.

All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. In one non-limiting embodiment, the terms are defined to be within 5%. The term "substantially" and its variations are defined as being largely but not necessarily wholly what is specified as understood by one of ordinary skill in the art, and in one non-limiting embodiment substantially refers to ranges within 0.01% to 5%.

While the specification concludes with the claims particularly pointing and distinctly claiming the invention, it is believed that the present invention will be better understood from the following description.

An embodiment of a composition for treating dry skin ("composition") includes therapeutically active concentrations of a mixture of skin protecting lipids in suitable oleaginous or aqueous vehicles. The composition is preferably in the form of an ointment (the terms "ointment" and "composition" are used interchangeably herein). However, in one or more embodiments, the composition can also be in the form of a gel.

The composition/ointment is intended for application on the skin surrounding the eyes, including, the eyelids, eyelid margins, and around the eye area (also referred to herein as the "ocular region"). The ointment can protect against and provide relief from dryness, irritation, and discomfort to the skin around the eye area by forming a protective, occlusive layer that can moisturize the skin and reduce inflammation and itching without stinging, burning, or stripping the skin.

The skin protecting lipids can include a lipid mixture comprising a sphingolipid in combination with one or more other lipids or oils. The sphingolipid provides the dual action of emollient and enhancement of healing by protection from inflammation. Sphingolipids are complex lipids which contain sphingosine or a related base, a polar headgroup and a long saturated or monounsaturated fatty acid connected to the backbone at its amino group. Sphingolipids can reinforce the skin barrier and regulate trans-epidermal water loss. In one embodiment, the total concentration of the sphingolipid in the composition is in the range of 0.25% to 1% w/w.

Preferably, the sphingolipid is selected from the group consisting of Phytosphingosine, Phytosphingosine HCl, dihydrosphingosine, sphingosine, sphingomyelins, glycosphingolipids and derivatives and mixtures thereof.

PSG is an active ingredient that is naturally present in the Stratum Corneum, the skin's outermost layer. PSG HCl is a salt of skin-identical PSG, and salicyloyl-PSG is a derivative of the skin-identical PSG which is covalently coupled with salicylic acid. PSG and its derivatives can inhibit the growth of microorganisms on the skin, reduce redness and inflamed skin by soothing the skin, and are active at very low concentrations. PSG is also a water-binding agent that mimics the natural lipid layer of the outer epidermis to increase the moisturizing of the skin. The use of PSG and its derivatives enhances the skin's barrier function which protects the skin from allergens and irritants and helps lock in moisture. Beneficially, PSG and its derivatives have both anti-bacterial and wound-healing properties, and they act as an active anti-inflammatory at concentrations as low as 0.1%.

Typically, the PSG concentration in skin care compositions is limited by solubility. While a higher concentration of PSG could enhance the overall effectiveness of a composition, an undissolved PSG mixture will cause further stinging, burning, or irritation to unhealthy skin. Thus, the primary challenge for novel PSG formulations for use around the eyes is the complete dissolution of the ingredient at elevated concentrations. In specific embodiments, the composition includes an elevated concentration, about 0.25% to about 1.0% w/w of PSG or PSG HCl. The inventors determined that a complete dissolution of these elevated levels of PSG/PSG HCl was promoted in an oleaginous base by the synergistic action of a hydrophilic cosolvent. Suitable hydrophilic solvents include glycerin, propylene glycol, and polyethylene glycol (for example, PEG 400 or 600), ethanol, isopropanol and derivatives and mixtures thereof. The hydrophilic solvents can be present in the composition in the range of about 1% to 5% by weight.

The one or more other lipids or oil increase the skin's hydration and strengthen the skin's protective barrier function thereby reducing dryness and irritation. The other lipids or oils can be selected, without limitation, from the group consisting of triglycerides, ceramides, glycolipids, phospholipids, mineral oil, squalane, sunflower oil, cottonseed oil, linseed oil and derivatives and mixtures thereof. A total concentration of each of the one or more other lipids is in the range of 15% to 30% w/w.

Triglycerides are an ester derived from glycerol and three fatty acids. They are one of the main constituents of body fat in humans and a major component of human skin oils. There are many types of triglycerides, including saturated and unsaturated types. Like other lipids, triglycerides can help reinforce the skin barrier, lock in moisture, and fight skin cell damage from the environment. In one or more embodiments, the ointment includes a triglyceride selected from the group consisting of castor oil, caprylic/capric triglyceride, ethyl oleate, isopropyl palmitate, isopropyl isostearate, isostearyl isostearate, argan oil, and mixtures thereof. In an exemplary embodiment, the ointment includes castor oil and PSG HCl.

Ceramides are waxy lipid molecules which are the main component of the stratum corneum of the epidermis layer of the skin. They play a vital role in the appearance of the skin and how the skin responds to the environment. Ceramides help hold skin together by forming a protective layer, thereby limiting moisture loss and protecting against pollution or other environmental stressors. Sphingolipids, and in particular phytosphingosine, can help the skin produce more ceramides.

Glycolipids are lipids with a carbohydrate link and derive from various plant and animal sources. Glycolipids, like ceramides, help maintain stability of the cell membrane. Glycolipids can be a good alternative to ceramides because ceramides are typically costly to extract or synthesize. Glycolipids are relatively easily extracted from plant sources and are consequently a cheaper solution while still maintaining similar efficacy to ceramides.

Phospholipids provide a barrier for the skin and seal in any active ingredients aimed at treating the skin. Phospholipids are a type of lipid molecule that are described as having hydrophilic heads and hydrophobic tails. This dual nature means that a phospholipid attracts water and absorbs it, which is a crucial component in keeping skin hydrated. Phospholipids provide a barrier for the skin and work much like a second skin by mimicking the skin's natural lipids to seal in any product added to the skin. In this way, phospholipids can help hydrating ingredients penetrate the skin and can ensure active ingredients are delivered deep into the skin. Moreover, phospholipids can help retain moisture thereby reducing skin dryness. Phospholipids are made up of two fatty acids, a phosphate group, and a glycerol molecule. Phospholipids are complex lipids, as distinguished from the simple lipids and other fat-soluble cell components.

The composition can also include a dermatologically acceptable vehicle to act as a diluent, dispersant, or carrier for the composition components, so as to facilitate distribution of the components when the composition is applied to the skin. The vehicle can be either an oleaginous vehicle (e.g., petrolatum, white petrolatum, yellow ointment, and white ointment) or an aqueous vehicle (e.g., distilled water and deionized (DI) water). Oleaginous vehicles have additional benefits of creating a physical barrier on the surface of skin to protect it from external aggressors and help prevent moisture loss. In specific embodiments, the vehicle in the composition can be white petrolatum or DI water. In an exemplary embodiment, the vehicle is white petrolatum. The white petrolatum is present in the composition in the range of about 65% to 75% by weight.

The ointment can further include an emulsifier selected from the group consisting of PEG-150 distearate, PEG-150 Pentaerythrityl Tetrastearate, Disteareth-75 IPDI, Glyceryl Stearate; PEG-100 Stearate, Ceteareth-20 and derivatives and mixtures thereof. The emulsifier (s) is/are present in the composition in the range of about 1% to 10% by weight.

The ointment can further include one or more moisturizing agents selected from the group consisting of isopropyl myristate, glycerin, propylene glycol, mineral oil, coconut oil, DL-panthenol, or mixtures thereof. The moisturizing agents can be broken down into three main categories: humectants (such as glycerin, propylene glycol, squalane and castor oil), emollients (such as caprylic/capric triglyceride, ethyl oleate, isopropyl palmitate, isopropyl isostearate, isostearyl isostearate, isopropyl myristate, and coconut oil), and occlusives (such as mineral oil, silicone oil and argan oil). Each of the three categories of moisturizing agents have different functions: humectants promote the retention of water due to the hygroscopic properties, emollients help smooth and soften the skin, and occlusives create a protective barrier on the skin to prevent the loss of moisture. A total concentration of the one or more emollients in the composition is each in the range of 0.01% to 10% w/w.

An organic solvent may be added to the composition to help dissolve components that are insoluble in the selected vehicle. Suitable organic solvents are alcohols with low molecular weights, such as isopropanol and ethanol. The low molecular weight alcohols can help the composition feel lighter on the skin, set quickly, and give a cooling effect.

The composition can further include one or more other components which are selected, without limitation, from the group consisting of surfactants, viscosity agents, preservatives, antioxidants, chelating agents, buffers, and mixtures thereof.

One or more surfactants can be used to help stabilize and emulsify the composition. The emulsifying property of surfactants would stabilize the composition by preventing the separation of the composition. Suitable surfactants are, preferably, nonionic surfactants, such as polysorbate 20, Brij 52, PEG-75 Lanolin, and TEGO Care 165 (Glyceryl Stearate (and) PEG-100 Stearate). Other exemplary surfactants can include sodium lauryl sulfate, alkoxy sulfonates, sodium lauryl ether sulfate, benzalkonium chloride, cetalkonium chloride and other surfactants.

Viscosity agents may be added to the composition to achieve a preferred viscosity. The viscosity agents may include, without limitation, carboxymethyl cellulose, hydroxypropyl methylcellulose, carbomers, and Sensogel™. The viscosity of the composition can be in the range of 10.0 to 50,000 cps.

The composition may include preservatives with antimicrobial properties to prevent damage to the composition caused by microorganisms. Suitable preservatives include, without limitation, phenoxyethanol, parabens (such as methylparaben, propylparaben and butylparaben), benzoic acid/sodium benzoate, sorbic acid/potassium sorbate, levulinic acid, and anisic acid.

Antioxidants may be added to the composition to protect it against damage and degradation caused by exposure to oxygen, and to protect the skin from the damaging effect of free radicals. The antioxidants may include, without limitation, polyphenols such as green tea extract and black tea extract, resveratrol, coenzyme Q10, and curcumin. The antioxidants can also include Tocopheryl acetate, D-α-Tocopheryl polyethylene glycol 1000 succinate or TPGS, butylated hydroxy toluene or BHT, butylated hydroxy anisole or BHA, propyl gallate, superoxide dismutase, tertiary butyllhydroguinone or TBHQ.

Chelating agents may be added to help stabilize the composition against the effects of metal contamination.

Chelating agents bind with metallic ions which prevents them from chemically reacting with any other components in the composition. Suitable chelating agents include, without limitation, ethylene diaminetetraacetic acid (EDTA), EDTA disodium, calcium disodium edetate, EDTA trisodium, albumin, transferrin, desferoxamine, desferal, desferoxamine mesylate, EDTA tetrasodium and EDTA dipotassium, or combinations of any of these.

Buffers may be added to the composition to adjust the pH to a desired level. The buffers can include citrate buffer, acetate buffer, phosphate buffer, borate buffer, Tris buffers, Histidine buffers, ammonium salt buffers. For example, the buffers may include, without limitation, sodium bicarbonate, acetic acid, adipic acid, boric acid, citric acid, glycolic acid, lactic acid, malic acid, uric acid, ammonium hydroxide, calcium hydroxide, magnesium hydroxide, sodium hydroxide, ammonium phosphate, calcium phosphate, potassium phosphate, sodium phosphate, dimethyl MeA, ethanolamine, triethanolamine, and tromethamine. The composition has a pH in the range of 3.0 to 9.0. Preferably, the pH range is from about 4 to about 8. High pH levels can make the skin dry and itchy, so it is important to keep the pH of the composition in the optimal range. If the product is alkaline or neutral, the stratum corneum (uppermost layer of the skin) is disrupted and in successive fashion damages the barrier (protective) function of the skin. This leads to dryness and decreases antibacterial defense and can increase skin sensitivity and inflammation. The skin leans towards a slightly acidic balance and thus applying a mildly acidic product can soothe the skin which allows for better moisture retention and strengthening of the skin barrier.

The composition can be formulated to be an ointment, gel, spray, cream, lotion, foam, or pre-moistened wipes. In preferred embodiments, the composition is formulated as viscous ointment or gel.

In an embodiment, the ointment can include about 15% to 30% castor oil, about 1%-10% PEG-150 distearate, about 1%-5% propylene glycol, about 0.25% to 1% Phytosphingosine HCl dissolved in about 65% to 75% white petrolatum. The ointment can further include viscosity agents, preservatives, antioxidants, chelating agents, buffers, surfactants, and mixtures thereof.

In another embodiment, the ointment contains: a sphingolipid (such as PSG or PSG HCl) at a concentration of 0.5-0.75% w/w; an oil (such as a medium chain triglyceride) at a concentration of 0.1-10% w/w; one or more moisturizing agents (such as propylene glycol, glycerin, and isopropyl myristate) each at a concentration of 0.1-7% w/w; a solvent (such as ethanol or isopropanol) at a concentration of 1-3.25% w/w; one or more surfactants (such as TEGO Care 165 and polysorbate 20) each at a concentration of 0.1-5% w/w; a viscosity agent (such as SensogelIM or hydroxypropyl methylcellulose) at a concentration of 1.5-5% w/w; one or more preservatives (such as phenoxyethanol, propylparaben, methylparaben, benzalkonium chloride, chlorobutanol, polyaminopropyl biguanide, poly-Lysine, phenylethyl alcohol, cetrimide, polquaternium preservatives) each at a concentration of 0.001-2% w/w; and a vehicle (such as white petrolatum or DI water) at a concentration that is necessary to reach 100% of the composition.

In one specific embodiment, the composition includes about: 0.25-1 wt % phytosphingosine or phytosphingosine HCl, 0.01-10 wt % medium chain triglyceride, 0.10 wt % propylene glycol, 0.10 wt % glycerin, 6 wt % isopropyl myristate, 2.5-3.25 wt % ethanol, 4 wt % TEGO Care 165, 0.10-0.50 wt % polysorbate 20, 1.5-5 wt % SensogelIM, 0.01-0.015 wt % propylparaben, 0.10 wt % methylparaben, and white petrolatum added up to 100 wt %.

In another specific embodiment, the composition includes about: 0.25-1 wt % phytosphingosine or phytosphingosine HCl, 0.01 wt % medium chain triglyceride, 1-7 wt % propylene glycol, 5 wt % propylene glycol, 3 wt % isopropyl myristate, 2.5 wt % ethanol, 1 wt % isopropanol, 5 wt % polysorbate 20, 3 wt % hydroxypropyl methylcellulose, 2 wt % phenoxyethanol, and DI water added up to 100 wt %.

Ingredient concentrations have been optimized to fully solubilize each within the formulation as opposed to a nonuniform suspension. Advantageously, the synergism of combining organic and hydrophilic cosolvents with an aqueous or oleaginous vehicle enables the dissolution of ingredients that are otherwise difficult to solubilize at elevated concentrations. For example, as described earlier, at high concentrations, PSG is hard to dissolve or disperse in purely aqueous or oleaginous vehicles and subsequently renders the composition gritty and irritating to the eyes. By optimizing the organic and hydrophilic cosolvents, and their respective concentrations, the present invention achieves a balance that fully solubilizes the formulation ingredients and promotes a user preferred texture.

The viscosity is in the range of 10.0 to 50,000 cps. The ointment has a pH between 3.0 and 9.0 and preferably between 4.0-7.0. In one or more embodiments, the ointment can be used as a makeup remover.

EXAMPLE

A small batch of the ointment having about 15% to 30% castor oil, about 1%-10% PEG-150 distearate, about 1%-5% propylene glycol, about 0.25% to 1% Phytosphingosine HCl, and about 65% to 75% white petrolatum by weight of the ointment was prepared as described below.

Phytosphingosine HCl and propylene glycol were mixed together in a beaker. The mixture was stirred using a stir bar on a stir plate at 500 RPM until fully dissolved. To aid dissolution, the mixture was further warmed to 50° C.

PEG-150-Distearate and Castor Oil were added to a larger container, preferably a final mix vessel. The container was heated to 70° C.±5° C. and the contents mixed, using an overhead mixer, with moderate agitation at approximately 500 RPM. While continuing to mix and heat, the Phytosphingosine HCl and propylene glycol mixture was added to the container. The mixing was continued until a uniform solution was formed.

The heating was then stopped, but the solution was continually mixed. Melted white petrolatum was then slowly added to the solution. This was followed by further mixing with high agitation at approximately 1000 rpm. The resulting ointment was then allowed to come to room temperature. The cooled ointment was then transferred to a clean, tared ointment container.

According to an embodiment, a method to protect against and provide relief from dryness, irritation, and discomfort on the eyelids, eyelid margins, and the area around the eyes, involves providing the composition according to the one or more embodiments disclosed herein. A therapeutically effective amount of the composition may be applied topically to intact skin on the effected eye areas to provide immediate and prolonged soothing action to dry skin. The composition may be applied for a set duration and frequency prescribed by a physician. The composition may also be administered to a patient in hospitals, doctor's offices, and home healthcare providers.

An ointment having castor oil, PEG-150 distearate, propylene glycol and Phytosphingosine HCl, in a white petrolatum base was studied for efficacy. Adult subjects with no known skin sensitivities or current skin conditions were enrolled in the study. The subjects were told to wash their hands and place a small 2 mm bead of the ointment to a clean fingertip. With their eyes closed, they were instructed to apply the ointment to the periorbital area. The subjects were given strict instructions to not apply the ointment directly in the eye. The subjects were instructed to apply the ointment as often as needed during the course of an eight-hour day, for a five day period, and asked to keep track of how many times they used the ointment during the day using a questionnaire. The questionnaire was designed to help evaluate the effectiveness of the ointment to provide temporary relief of dryness and irritation of the eyelid and eye areas. The questionnaire covered two aspects: the use of the product, and the product experience in terms of being soothing, moisturizing, softening, and non-irritating. At the end of the five day study period, the questionnaire was evaluated by a professional evaluator. The results can be summarized as follows. Sixteen subjects completed the study. A majority of the respondents had a positive review of the product and 100% agreed that the product was soothing, moisturizing and softening. Over 90% of the subjects indicated the product was non-irritating. The study design, questionnaire, patient screening and results compilation were done by a compounding pharmacy in Texas.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only.

We claim:

1. A composition for treating dry skin, comprising:
   an oleaginous base;
   a lipid mixture, the lipid mixture comprising a sphingolipid and at least one oil wherein the at least one oil is selected from the group consisting of castor oil, caprylic/capric triglyceride, ethyl oleate, isopropyl myristate, isopropyl palmitate, isopropyl isostearate, isostearyl isostearate, argan oil, and derivatives and mixtures thereof; and
   a hydrophilic solvent; and
   an emulsifier, wherein the emulsifier is selected from the group consisting of PEG-150 distearate, PEG-150 Pentaerythrityl Tetrastearate, Disteareth-75 isophorone diisocyanate and derivatives and mixtures thereof, and wherein the composition is in the form of an ointment or gel.

2. The composition according to claim 1, wherein the oleaginous base comprises white petrolatum.

3. The composition according to claim 2, wherein the white petrolatum is present in the composition in the range of about 65% to 75% by weight.

4. The composition according to claim 1, wherein the sphingolipid is selected from the group consisting of Phytosphingosine, Phytosphingosine HCl, dihydrosphingosine, sphingosine, sphingomyelins, glycosphingolipids and derivatives and mixtures thereof.

5. The composition according to claim 1, wherein the sphingolipid is present in the composition in the range of about 0.25% to 1% by weight.

6. The composition according to claim 1, wherein the at least one oil is present in the composition in the range of about 15% to 30% by weight.

7. The composition according to claim 1, wherein the hydrophilic solvents is selected from the group consisting of glycerin, propylene glycol, and DL-panthenol and derivatives and mixtures thereof.

8. The composition according to claim 1, wherein the hydrophilic solvents is present in the composition in the range of about 1% to 5% by weight.

9. The composition according to claim 1, wherein the emulsifier is present in the composition in the range of about 1% to 10% by weight.

10. A composition for treating dry skin, comprising:
    a white petrolatum base;
    a lipid mixture, the lipid mixture comprising Phytosphingosine HCl and castor oil;
    propylene glycol; and
    PEG-150 distearate.

11. The composition according to claim 10, wherein the white petrolatum is present in the composition in the range of about 65% to 75% by weight.

12. The composition according to claim 10, wherein the Phytosphingosine HCl is present in the composition in the range of about 0.25% to 1% by weight.

13. The composition according to claim 10, wherein the castor oil is present in the composition in the range of about 15% to 30% by weight.

14. The composition according to claim 10, wherein the propylene glycol is present in the composition in the range of about 1% to 5% by weight.

15. The composition according to claim 10, wherein the PEG-150 distearate is present in the composition in the range of about 1% to 10% by weight.

* * * * *